United States Patent [19]

Picha et al.

[11] Patent Number: 5,084,014
[45] Date of Patent: Jan. 28, 1992

[54] PACKAGE FOR INITIAL PLACEMENT OF LOW PROFILE GASTROSTOMY DEVICE AND METHOD OF PLACEMENT

[75] Inventors: George J. Picha, Independence; Dean J. Secrest, Euclid, both of Ohio

[73] Assignee: Applied Medical Technology, Inc., Independence, Ohio

[21] Appl. No.: 626,969

[22] Filed: Dec. 13, 1990

[51] Int. Cl.⁵ .............................................. H61M 5/00
[52] U.S. Cl. .................................... 604/54; 206/438; 604/175
[58] Field of Search .................. 604/171, 175, 54; 206/363, 438, 497

[56] References Cited

U.S. PATENT DOCUMENTS

| | | | |
|---|---|---|---|
| 3,934,721 | 1/1976 | Juster et al. | 604/171 |
| 4,062,363 | 12/1977 | Bonner, Jr. | 604/171 |
| 4,551,137 | 11/1985 | Osborne | 604/171 |
| 4,758,219 | 7/1988 | Sacks et al. | 604/54 |
| 4,850,953 | 7/1989 | Haber et al. | |
| 4,863,438 | 9/1989 | Gauderer et al. | |
| 4,944,732 | 7/1990 | Russo | 604/175 |
| 4,986,810 | 1/1991 | Semrad | 604/175 |

OTHER PUBLICATIONS

Percutaneous Endoscopic Gastrostomy: A Nonoperative Technique for Feeding Gastrostomy, by-Jeffrey L. Ponsky, MD & Michael W. L. Gauderer, MD, Gastrointestinal Endoscopy-copyright 1981, vol. 27, No. 1, 1981.
The Gastrostomy "Button"-A Simple, Skin-Level, Nonrefluxing Device for Long-Term Enteral Feedings, by-Michael W. L. Gauderer, George J. Picha & Robert J. Izant, Jr., Journal of Pediatric Surgery-copyright 1984, vol. 19, No. 6 (Dec.) 1984.

Primary Examiner—Paul J. Hirsch
Attorney, Agent, or Firm—Pearne, Gordon, McCoy & Granger

[57] ABSTRACT

A low profile or skin level gastrostomy device for initial endoscopic placement in an incision provided through the stomach and abdominal walls of a patient has a collapsed resilient end portion packaged and compressed within a shroud that allows the end portion of the device positioned within the stomach to easily pass from the inner to the outer end of the incision. The shroud is pulled or pushed outwardly through the incision until the device is properly positioned therein. Subsequent to device placement, the shroud is removed and discarded, allowing the now external end portion of the device to expand to its normal position so as to engage the outer surface of the abdominal wall to maintain the device in position. Such a gastrostomy device package and method of placement avoid the need for establishing a fistulas stoma tract before placement of a low profile gastrostomy device, as is the usual case.

15 Claims, 4 Drawing Sheets

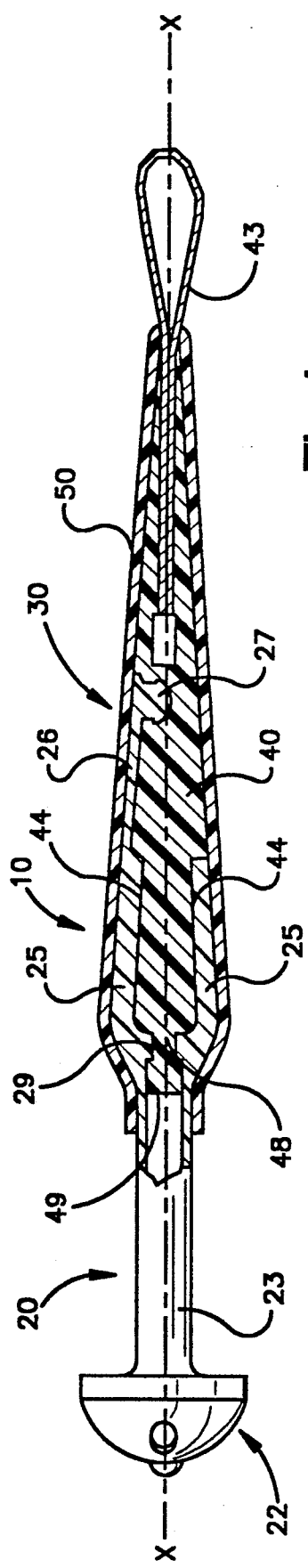
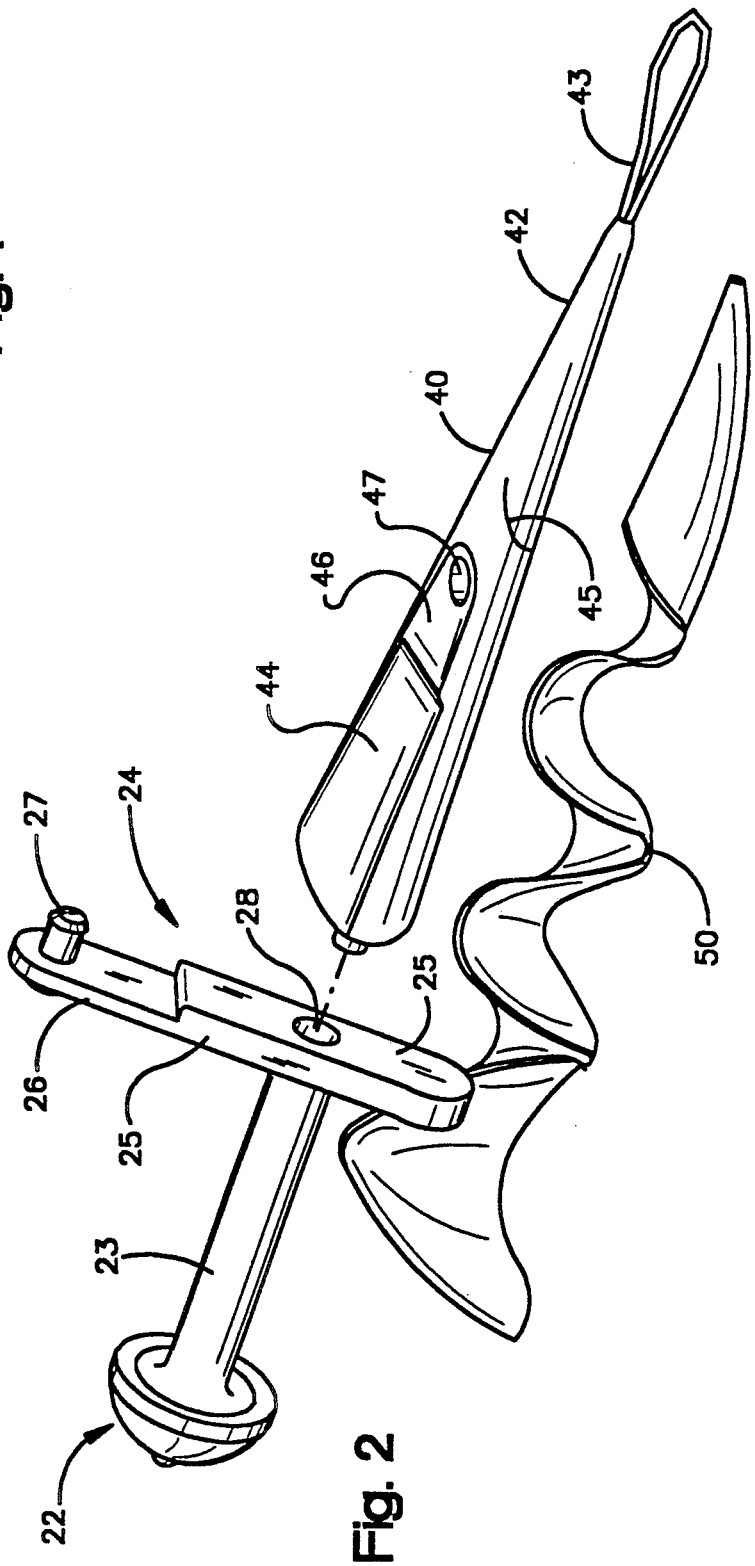

PACKAGE FOR INITIAL PLACEMENT OF LOW PROFILE GASTROSTOMY DEVICE AND METHOD OF PLACEMENT

BACKGROUND OF THE INVENTION

The present invention relates in general to gastrostomies providing long term enteral feeding and, more particularly, to a gastrostomy device packaging technique and installation method for initially placing a low profile gastrostomy device in a patient without first establishing a fistulas stoma tract as heretofore required by the prior art.

Low profile or skin level gastrostomy devices and the advantages attendant to their use are known in the art, as exemplified by U.S. Pat. No. 4,863,438, the entirety of which is incorporated herein by reference. This patent, assigned to the assignee of the present invention, discloses a gastrostomy device having an intragastric end located within a body cavity such as the stomach of the patient, a tubular midportion extending from the intragastric end outwardly through the stomach and abdominal walls, and an external low profile end having a pair of winglike projections that engage the outer surface or skin of the patient's abdominal wall to maintain the gastrostomy device in proper position for intermittently receiving a conventional enteral feeding tube projecting into the stomach.

Such a prior art device is often referred to as a "replacement" gastrostomy device, since it is substituted for the usual gastrostomy tube that is initially placed in a patient for six to eight weeks until a fistulas stoma tract is established. Once the stoma tract is established, the gastrostomy tube is removed, and the "replacement" gastrostomy device is inserted into the stoma tract.

It is a goal of the present invention to eliminate the need for first establishing a fistulas stoma tract prior to installation of a low profile gastrostomy device of the type disclosed in the earlier-noted patent. By eliminating the use of a gastrostomy tube to establish the stoma tract, medical costs associated therewith can be eliminated. Also, initial placement of a low profile gastrostomy device allows the patient to immediately benefit from the advantages inherent in the use of a low profile gastrostomy device as opposed to a gastrostomy tube.

SUMMARY OF THE INVENTION

In accordance with the present invention, a gastrostomy device package is provided to permit initial placement of a low profile gastrostomy device in an incision extending from outside a living body into an internal body cavity such as a stomach. The gastrostomy device includes a tubular mid-portion having an inner end providing an intragastric portion and an outer end providing a collapsible external portion. A shroud means surrounds and encloses the external portion to maintain it in a collapsed condition within the shroud means. The shroud means facilitates movement of the external portion of the gastrostomy device through the incision and is removable to allow the external portion to expand to a normal uncollapsed condition subsequent to the placement of the gastrostomy device in the incision.

Preferably, the shroud means is elongated and has a distal end that is at least partially tapered to function as a dilator, facilitating movement of the shroud through the incision from the internal body cavity outwardly to the external surface of the body. In one embodiment, the tapered distal end of the shroud is provided with a wire loop so that it can be pulled outwardly through the incision. In another embodiment, the tapered distal end is provided with a longitudinally extending bore that can receive a guidewire so that the distal end can be pushed outwardly through the incision.

Preferably, at least the external portion of the gastrostomy device is formed of resilient elastomeric material, such as biocompatible silicone rubber, so that it can be easily collapsed and compressed within the shroud means. The external portion includes at least two winglike projections extending radially away from the longitudinal axis of the gastrostomy device. When being retained within the shroud means, the winglike projections are folded towards each other so that they lie along generally parallel lines adjacent to and bracketing the longitudinal axis. A sleeve of plastic film material constituting a part of the shroud means extends over the winglike projections to retain them in their collapsed condition. After the gastrostomy device package is properly positioned within the incision, the plastic film is cut and peeled away so that the winglike projections can move to their normal laterally extending positions so as to engage the outer surface or skin of the body, thereby retaining the gastrostomy device in its proper position.

In further accordance with the invention, a method of placing a gastrostomy device of the above-noted type includes the steps of providing an incision extending from the external surface of a living body to an inner body cavity such as the stomach, positioning within said cavity a gastrostomy device package as noted above, inserting the shroud means of the gastrostomy device into the incision and moving the shroud means from the inner end of the incision out through the outer end thereof so as to position the tubular midportion of the device within the incision, and then removing the shroud means to allow the external portion to expand to a normal uncollapsed condition so that the now expanded external portion engages the outer surface of the body to maintain the gastrostomy device in position. In practicing the method of placing the gastrostomy device, the shroud can either be pulled through the incision or pushed through the incision, depending upon the type of gastrostomy device package utilized, as noted above.

BRIEF DESCRIPTION OF THE DRAWINGS

A fuller understanding of the invention may be had by referring to the following description and claims, taken in conjunction with the accompanying drawings, wherein:

FIG. 1 is a longitudinal, partial, cross-sectional view of a first embodiment of a gastrostomy device package in accordance with the present invention;

FIG. 2 is an exploded view of the gastrostomy device package of FIG. 1;

DETAILED DESCRIPTION OF THE PREFERRED EMBODIMENTS

Figure 3C:
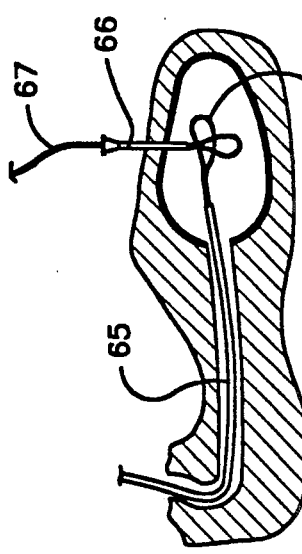
FIGS. 3A-3F sequentially illustrate the methodology for placing the gastrostomy device of FIGS. 1 and 2 in an incision in a living body, such as a human being.

With reference to FIGS. 1 and 2, a first embodiment of a gastrostomy device package in accordance with the present invention is illustrated. The package 10 is generally elongated so as to extend along a longitudinal axis x—x, as illustrated. The package 10 is comprised of two major portions, namely, a low profile gastrostomy device 20, often referred to in the art as a "gastrostomy button," and a shroud means 30 comprised primarily of a dilator member 40, and a plastic film material 50 constituting a tubular sleeve extending generally completely over the dilator 40. The gastrostomy device 20 illustrated is of the type disclosed in earlier incorporated U.S. Pat. No. 4,863,438. The device 20 includes an intragastric portion 22 located at one end of a tubular midportion 23 having at its other end a resilient external portion 24. The device 22 is preferably formed of biocompatible silicone rubber material so as to be flexible and elastomeric. The length of the tubular portion is sized to be dimensionally compatible with the combined thickness of, for example, a patient's stomach and abdominal walls.

The external portion 24 of the gastrostomy device 20 includes a pair of diametrically opposed winglike projections 25, one of which has extending from it a plug retainer 26 which has a distal end providing a plug 27, wherein the plug retainer 26 can be folded over to permit insertion of the plug 27 into a feeding tube receptor port 28. As is known in the art, when positioned within, for example, a human or animal patient undergoing medical treatment, an enteral feeding tube can be inserted into port 28 through the tubular midportion 23 and into the intragastric portion 22 to effect the flow of fluid either into or out of a body cavity, such as the patient's stomach, within which the intragastric portion is located. It is to be noted that the intragastric portion 22 includes within it the usual normally closed reflux valve (not shown) which prevents egress of fluid outwardly through the tubular portion 23 when the enteral feeding tube is not maintaining the valve in an open position.

With particular reference to FIG. 1, the flexible winglike projections 25, including the associated plug retainer 26 and plug 27, are shown in a folded or collapsed condition so that they extend along parallel lines adjacent to the axis x—x, as illustrated. The dilator 40 provides a pair of opposed flats or recesses 44 against which the winglike projections 25 are held in their folded or collapsed position by the plastic film 50 in the preferred form of a tubular sleeve of heat-shrink or shrink-wrap type plastic film. In its collapsed condition, the external portion 24 (FIG. 2) is contained within and compressed by the shroud means 30, and, more specifically, the plastic film 50. It is to be noted that, while the winglike projections 25 of FIG. 1 are shown folded and extending toward the right, they could also be folded toward the left against opposite sides of tubular midportion 23 and held in place by extending the plastic film 50 leftward to overlap them and maintain them in a collapsed condition. The dilator member 40 further includes a plug retainer recess or flat 46 having a plug recess 47 into which the plug 27 fits, as illustrated in FIG. 1. It is contemplated that the plug retainer 26 and plug 27 could be eliminated and, instead, a separate plug structure could be provided after placement of the device 20 in a patient, as will become apparent. The dilator member 40 has a tapered distal end 42 which is provided with a pull wire loop 43 embedded within the dilator member, as illustrated.

With further reference to FIG. 1, the dilator 40 is also provided with a reduced diameter portion 48 which forms an inboard part of a retainer tip 49 that extends and snaps into the external end 24, i.e., port 28, of the tubular portion 23, as illustrated. The gastrostomy device 20 is provided with an annular or circular lip 29 that fits into the reduced diameter portion 48, constituting a circular groove, so as to provide a releasable locking means holding the gastrostomy device 20 in position relative to the dilator 40. It can also be seen that an open, or leftward end as viewed in FIG. 1, of the plastic film 50 constituting a tubular sleeve extends beyond and over both the circular lip 29 and its associated annular groove constituted by reduced diameter portion 48, so as to hold and compress the circular lip 29 into the reduced diameter portion 48 of the dilator 40.

With reference to FIG. 2, a guide groove 45 is provided, as illustrated, on a surface of the dilator member 40 spaced from the external end portion 24 of the gastrostomy device 20 when in its position as illustrated in FIG. 1. The guide groove provides an indicator point for partially cutting the plastic film 50 and peeling it around and away from the dilator member 40, as illustrated in FIG. 2, so that the gastrostomy device 20 and the dilator member 40 can be separated from each other so as to allow the resilient winglike projections 25 to return to a normal expanded position as illustrated in FIG. 2.

Thus, FIG. 1 illustrates a gastrostomy device package for initial placement of the gastrostomy device 20 in a patient, as discussed below, while FIG. 2 illustrates the package in a disassembled form after the device has been placed within an incision in the patient, as will now be discussed.

With reference to FIGS. 3A-3F, a method of placing in a patient the gastrostomy device as illustrated and discussed with regard to FIGS. 1 and 2 will now be set forth.

Figure 3F:
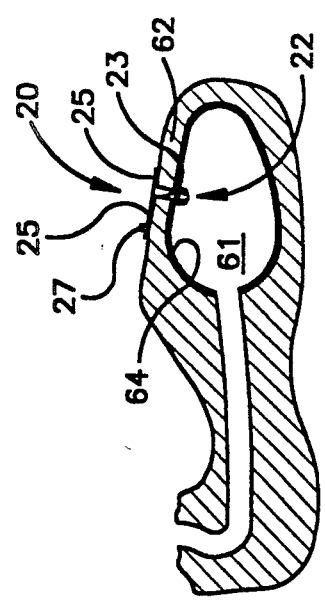
Figure 3B:
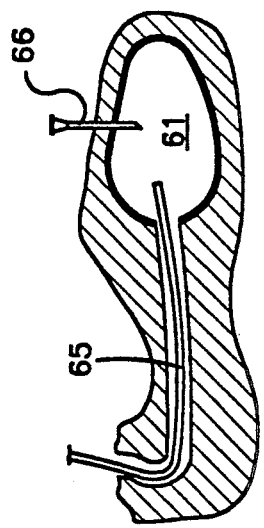
Figure 3E:
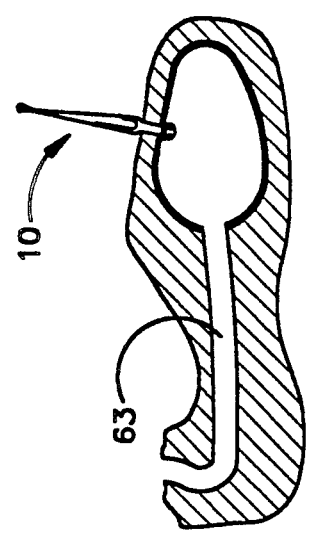
Figure 3A:
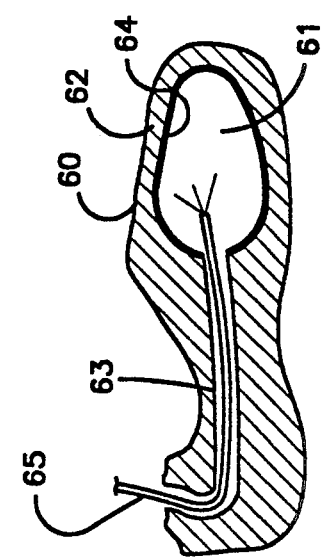

Turning to FIG. 3A, there is schematically illustrated a patient having an inner body cavity such as a stomach 61 within which is to be placed the gastrostomy device in accordance with the present invention. It is to be noted that the gastrostomy device package and method of placement disclosed and claimed herein can be used for inserting a gastrostomy device into other viscera of the body for other applications, such as, for example, urinary bladder drainage, ileostomy, jejunostomy, and cystostomy.

The outer surface 60 or skin of the patient extends over an abdominal wall 62, which in turn abuts the stomach wall 64. In a first step for placing the gastrostomy device package discussed earlier, the stomach 61 of the patient is insufflated via an endoscope tube 65 extending down through the esophagus 63 of the patient, as illustrated. As illustrated in FIG. 3B, a conventional trocar needle 66 is inserted through the abdominal and stomach wall of the patient to establish an incision that will receive a gastrostomy button.

Figure 3D:
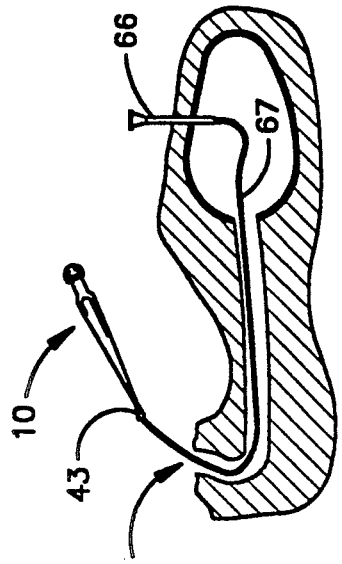

As shown in FIG. 3C, a pull wire 67 is inserted down through the trocar needle 66 so that its end can be captured by a snare 68 extending through the endoscope tube 65. With further reference to FIG. 3D, the pull wire 67 has been pulled outwardly through the patient's mouth 69 so that the pull wire 43 of the gastrostomy device package can be attached, as illustrated. Turning to FIG. 3E, the gastrostomy device package 10, by use of the pull wire 67, has been pulled down the esophagus 63 of the patient, and then through the incision provided by the trocar needle 66. At this point, the shroud means 30 (see FIGS. 1 and 2) is removed.

Turning to FIG. 3F, and as earlier discussed with regard to FIG. 2, the intragastric portion 22 of the gastrostomy device 20 is now located within the stomach 61 of the patient, while the tubular midportion extends through the stomach wall 64 and abdominal wall 62, with the winglike projections 25 in their extended, uncollapsed, normal position engaging the outer surface 60 of the abdominal wall 62, wherein the gastrostomy device 20 is now retained in position.

By use of the gastrostomy device package illustrated in FIGS. 1 and 2 and the methodology for placing it as illustrated in FIGS. 3A-3F, the use of the traditional gastrostomy tube to establish a fistulas stoma tract is avoided. Thus, the cost and patient trauma associated therewith are eliminated, and the benefits afforded by the low profile gastrostomy device 20 are available at an earlier point in time to the patient requiring a gastrostomy.

Figure 4:
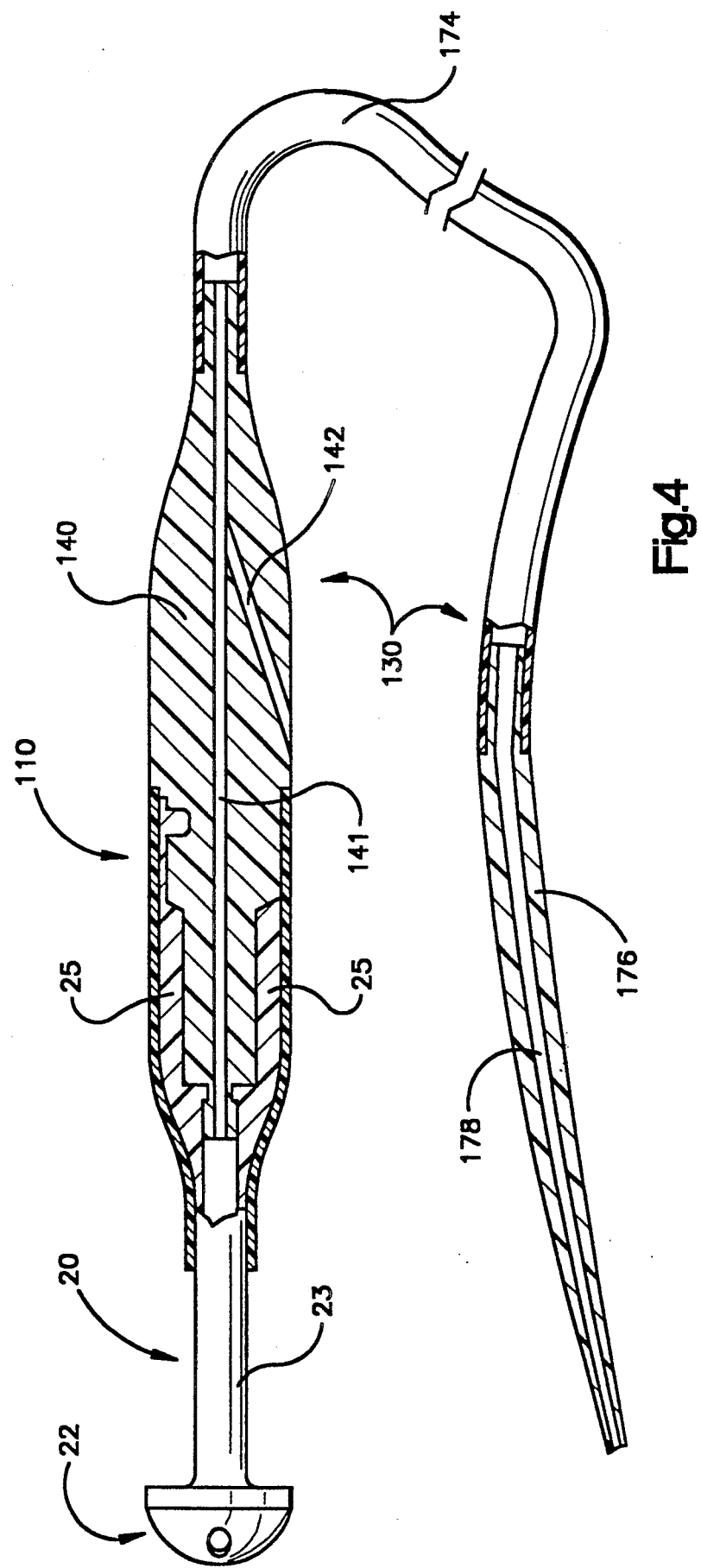
FIG. 4 is a longitudinal, partial, cross-sectional view of a second embodiment of a gastrostomy device package in accordance with the present invention.

Turning to FIG. 4, another embodiment of the present invention is illustrated. An alternative gastrostomy device package 110 can also be used for initial placement of the gastrostomy device 20, which is identical to that illustrated in FIGS. 1 and 2. As shown in FIG. 4, an alternative shroud means 130 includes additional components to permit installation of the gastrostomy device 20 by use of a guidewire type method of the type disclosed in U.S. Pat. No. 4,758,219, incorporated herein by reference in its entirety.

As contrasted to the gastrostomy device package 10 illustrated in FIGS. 1 and 2, a tapered dilator member 140 has extending longitudinally through it a bore 141 that is of a diameter that will accept a guidewire (to be subsequently illustrated). A secondary or lateral bore 142 extending between the central bore 141 and the exterior of the dilator 140 as illustrated provides an alternative guidewire path so as to avoid passing a guideware through the gastrostomy device 20, as may be desirable in some cases. The distal end of the dilator member 140 is connected to one end of a flexible guide tube 174. The other end of the guide tube 174 is provided with a tapered dilator tip 176 having a central bore 178. Thus, the shroud means 130 of the embodiment of the invention illustrated in FIG. 4 includes the dilator member 140, the guide tube 174, and the dilator tip 176. The shroud means 130 also includes a tubular sleeve of shrink-wrap type plastic film 150, serving the same function in terms of retention of the winglike projections 25 as discussed earlier with regard to FIGS. 1 and 2. It can be seen that the dilator member 140 has a tapered outer surface portion extending toward the guide tube 174 to which it is connected. Also, the dilator tip 176 is tapered to a point. These sequential tapers facilitate movement of the shroud means 130 from the inward to the outward end of an incision in a patient, as will now be further illustrated with regard FIGS. 5A-5F.

Figure 5A:
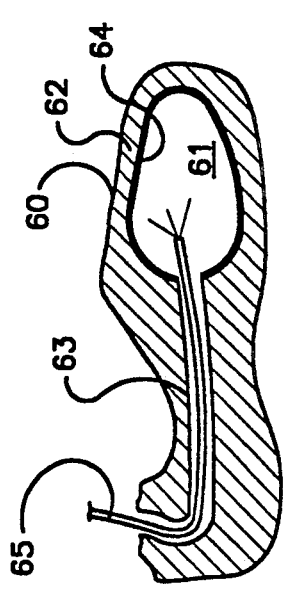
FIGS. 5A-5F sequentially illustrate the methodology for placing the gastrostomy device of FIG. 4 in an incision in a living body, such as a human being.
Figure 5B:
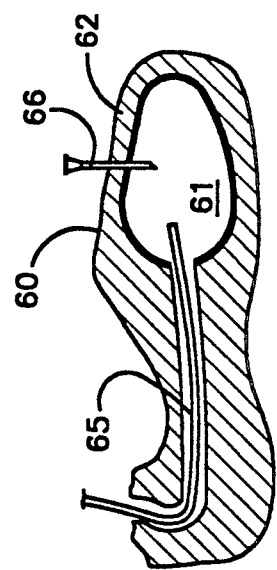
Figure 5C:
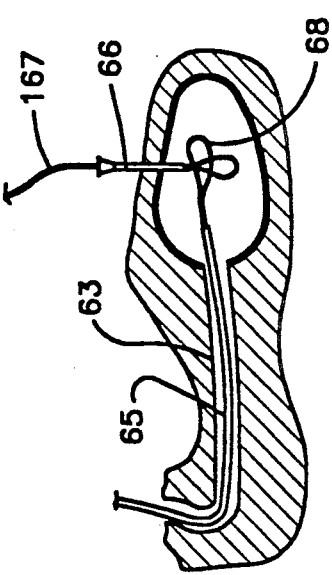

With reference to FIG. 5A, an endoscope tube 65 inserted into the esophagus 63 of the patient is used to insufflate the stomach 61 so that the stomach wall 64 is held tightly against the abdominal wall 62. Turning to FIG. 5B, a conventional trocar needle 66 is used to establish an incision from the outer surface 60 of the abdominal wall 62 into the stomach 61. As shown in FIG. 5C, a guidewire 167 is fed down through the trocar needle and then retrieved by a snare 68, wherein the endoscope tube 65 with guidewire 167 is withdrawn from the esophagus 63.

Figure 5D:
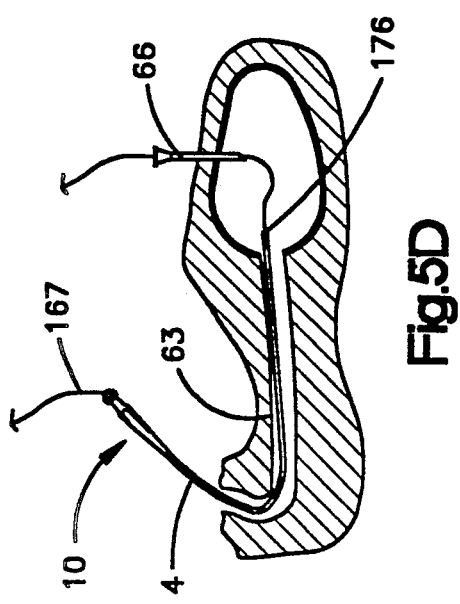

As shown in FIG. 5D, the guidewire 167 extends through the trocar needle 66, through the patient's esophagus 63, and out of the patient's mouth. The gastrostomy device package 110 is then, in effect, threaded over the guidewire 167, using either central bore 141 or lateral bore 142, and then pushed downwardly along the guidewire 167 through the esophagus 63 of the patient so that the dilator tip 176 and its associated flexible guide tube 174 are pushed outwardly through the incision in the abdominal wall of the patient.

Figure 5E:
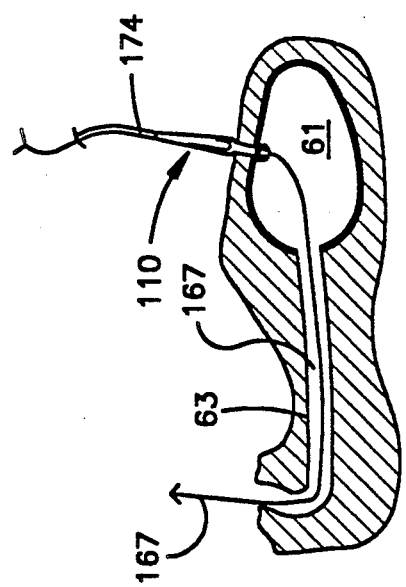
Figure 5F:
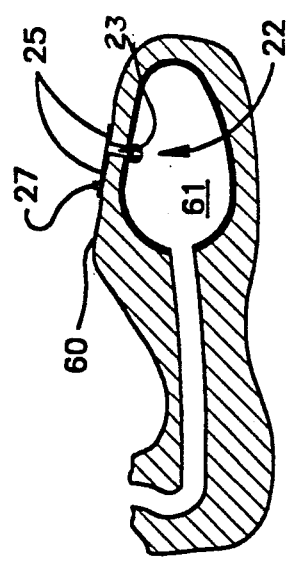

With reference to FIG. 5E, the guide tube 174 has been pushed and then pulled completely through the incision, which now retains the gastrostomy device package 110, as illustrated. At this point, and as discussed earlier in connection with FIG. 4, the shroud means 130 is then removed by cutting and peeling away plastic material 150 so that, as shown in FIG. 5F, the winglike projections 25 will expand to their normal position so as to engage the outer surface 60 or skin of the patient, whereby the tubular midportion 23 extends through the abdominal wall of the patient, the intragastric portion 22 being maintained in its desired position within the patient's stomach 61.

From the foregoing, it may be seen that the two embodiments of the gastrostomy device package illustrated in FIGS. 1, 2 and 4 and their associated methodologies of placement illustrated in FIGS. 3A-3F and FIGS. 5A-5F provide for initial placement of a low profile gastrostomy device.

It should be evident that this disclosure is by way of example, and that various changes may be made by adding, modifying or eliminating details without departing from the fair scope of the teaching contained in this disclosure. The invention is therefore not limited to the particular details of the disclosure except to the extent that the following claims are necessarily so limited.

What is claimed is:

1. A gastrostomy device package comprising:
    a gastrostomy device with a tubular midportion having an inner end providing an intragastric portion locatable in an internal cavity of a living body, and an outer end providing a collapsible external portion locatable at the outer surface of said living body, and
    a shroud means surrounding and enclosing said external portion to maintain said external portion in a collapsed condition within said shroud means, said shroud means being removable to allow said external portion to expand to a normal uncollapsed condition subsequent to the placement of the gastrostomy device in said living body.

2. A package according to claim 1, wherein the shroud means is elongated and has a distal end that is at least partially tapered.

3. A package according to claim 2, wherein said distal end is provided with a wire loop.

4. A package according to claim 2, wherein said distal end is provided with a longitudinal bore extending therethrough for receiving a guidewire along which said distal end can be moved.

5. A package according to claim 1, wherein said collapsed external portion is compressed within said shroud means.

6. A package according to claim 1, wherein said external portion is formed of resilient elastomeric material.

7. A package according to claim 1, wherein said shroud means includes a heat shrinkable plastic film material constituting a shrink-wrap package containing said external portion.

8. A gastrostomy device package comprising:

a gastrostomy device with an elongated tubular midportion coaxially extending along a longitudinal axis, said midportion having an inner end providing an intragastric portion locatable in an internal cavity of a living body, and an outer end providing a collapsible external portion locatable at the outer surface of said living body, said external portion including at least two wing-like projections extending radially away from said axis when said external portion is in a normal uncollapsed condition; and a shroud means including a tubular sleeve of plastic film material surrounding and enclosing said external portion to maintain said external portion in a collapsed condition within said sleeve wherein said projections extend along lines generally parallel to said longitudinal axis so that the lateral extension of said external portion is reduced, said sleeve being removable to allow said projections to expand and extend radially away from said axis when said external portion is in a normal uncollapsed condition subsequent to the placement of the gastrostomy device in said living body.

9. A package according to claim 8, wherein said projections are in adjacent, generally parallel relationship with each other when said external portion is in a collapsed condition within said sleeve.

10. A package according to claim 8, wherein said projections are diametrically opposed to each other relative to said longitudinal axis.

11. A package according to claim 8, wherein said projections are formed of resilient elastomeric material.

12. A method of placing a gastrostomy device in a living body, comprising the steps of:

providing an incision extending from the external surface of the body to an inner body cavity;

positioning within said cavity a gastrostomy device with a tubular midportion having an inner end providing an intragastric portion, and an outer end providing a collapsible external portion, a shroud means surrounding and enclosing said external portion to maintain said external portion in a collapsed unexpanded condition within said shroud means;

inserting the shroud means into said incision and moving the shroud means from the inner end of the incision out through the outer end thereof so as to position said tubular midportion within said incision with said intragastric portion remaining in said body cavity; and removing said shroud means to allow said external portion to expand to a normal uncollapsed condition so that the now expanded external portion engages the outer surface of the body to maintain the gastrostomy device in position.

13. A method according to claim 12, wherein said removing is accomplished by cutting and peeling away said shroud means.

14. A method according to claim 12, including providing a wire loop at a distal end of said shroud means, said wire loop with the shroud means attached being pulled through said incision from its inner to its outer end to position said midportion within said incision.

15. A method according to claim 12, including providing a bore extending through said shroud means, providing a guidewire extending through said bore and said incision, and pushing said shroud means along said guidewire and through said incision from its inner to its outer end to position said midportion within said incision.

* * * * *